US012014495B2

(12) United States Patent
Oktay et al.

(10) Patent No.: US 12,014,495 B2
(45) Date of Patent: Jun. 18, 2024

(54) GENERATING REPORTS FROM SCANNED IMAGES

(71) Applicant: Microsoft Technology Licensing, LLC, Redmond, WA (US)

(72) Inventors: Ozan Oktay, London (GB); Javier Alvarez-Valle, Cambridge (GB); Melanie Bernhardt, Cambridge (GB); Daniel Coelho De Castro, Cambridge (GB); Shruthi Jaisimha Bannur, Cambridge (GB); Anton Schwaighofer, Cambridge (GB); Aditya Nori, Cambridge (GB); Hoifung Poon, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 447 days.

(21) Appl. No.: 17/484,882

(22) Filed: Sep. 24, 2021

(65) Prior Publication Data
US 2023/0102428 A1    Mar. 30, 2023

(51) Int. Cl.
*G06T 7/00*     (2017.01)
*G06F 3/04842*  (2022.01)
(Continued)

(52) U.S. Cl.
CPC ........ *G06T 7/0012* (2013.01); *G06F 3/04842* (2013.01); *G06F 40/166* (2020.01);
(Continued)

(58) Field of Classification Search
CPC ... G06T 7/0012; G06T 11/001; G06T 11/203; G06T 2207/10088; G06T 2207/10104;
(Continued)

(56) References Cited

U.S. PATENT DOCUMENTS

| 10,452,813 B2 | 10/2019 | Sorenson et al. |
| 11,004,559 B2 | 5/2021 | Stoval et al. |

(Continued)

FOREIGN PATENT DOCUMENTS

| EP | 3675130 A1 | 7/2020 |
| WO | 2014197669 A1 | 12/2014 |

(Continued)

OTHER PUBLICATIONS

"Backpropagation", Retrieved From: https://en.wikipedia.org/wiki/Backpropagation, Jul. 8, 2021, 8 Pages.

(Continued)

*Primary Examiner* — Md K Talukder
(74) *Attorney, Agent, or Firm* — Barta Jones, PLLC

(57) ABSTRACT

A computer implemented method comprising: receiving a report on a condition of a human or animal subject, composed by a user based on a scan of the subject; inputting the current report and the scan into a trained machine learning model; and based on the report and the scan, the machine learning model generating one or more suggestions for updating the text of the report. The method further comprises causing a user interface to display to the user one or more suggestions for updating the text of the report, with each respective suggestion visually linked in the user interface to a corresponding subregion within at least one image of the scan based upon which the respective suggestion was generated.

20 Claims, 5 Drawing Sheets

(51) Int. Cl.
  *G06F 40/166* (2020.01)
  *G06N 20/00* (2019.01)
  *G06T 11/00* (2006.01)
  *G06T 11/20* (2006.01)

(52) U.S. Cl.
  CPC ............ *G06N 20/00* (2019.01); *G06T 11/001* (2013.01); *G06T 11/203* (2013.01); *G06T 2207/10088* (2013.01); *G06T 2207/10104* (2013.01); *G06T 2207/10116* (2013.01); *G06T 2207/10132* (2013.01); *G06T 2207/20081* (2013.01)

(58) Field of Classification Search
  CPC . G06T 2207/10116; G06T 2207/10132; G06T 2207/20081; G06F 3/04842; G06F 40/166; G06F 40/117; G06F 40/30; G06F 40/134; G06F 40/169; G06F 40/216; G06F 40/284; G06N 20/00; G06N 3/045; G06N 3/084; G16H 30/40; G16H 50/20; G16H 15/00
  See application file for complete search history.

(56) References Cited

U.S. PATENT DOCUMENTS

| | | | |
|---|---|---|---|
| 11,087,460 | B2 | 8/2021 | Buckler et al. |
| 11,222,717 | B2 | 1/2022 | Lyman et al. |
| 11,894,114 | B2* | 2/2024 | Paik ........................ G16H 15/00 |
| 2011/0270123 | A1* | 11/2011 | Reiner .................... A61B 6/469 600/558 |
| 2017/0337329 | A1 | 11/2017 | Liu et al. |
| 2018/0204325 | A1 | 7/2018 | Steigauf et al. |
| 2019/0150857 | A1 | 5/2019 | Nye et al. |
| 2020/0085382 | A1 | 3/2020 | Taerum et al. |
| 2020/0334566 | A1 | 10/2020 | Vianu et al. |
| 2020/0395111 | A1* | 12/2020 | Forzoni ............... G10L 15/1815 |
| 2020/0411173 | A1 | 12/2020 | Mansi et al. |
| 2021/0110912 | A1* | 4/2021 | Mukherjee ............. G06F 40/253 |
| 2021/0366106 | A1* | 11/2021 | Yao ...................... G06F 21/6254 |
| 2023/0335261 | A1* | 10/2023 | Reicher ................... G16H 30/20 |
| 2024/0006039 | A1* | 1/2024 | Ferrando ............... G06F 40/174 |

FOREIGN PATENT DOCUMENTS

| | | |
|---|---|---|
| WO | 2021067624 A1 | 4/2021 |
| WO | 2021142209 A1 | 7/2021 |

OTHER PUBLICATIONS

"Federal Rules Mandating Open Notes", Retrieved From: https://www.opennotes.org/onc-federal-rule/, Apr. 26, 2021, 8 Pages.

"Increasing the Value of Radiology Reports", Retrieved From: https://www.siemens-healthineers.com/en-uk/news/mso-structured-reporting.html, Nov. 9, 2017, 11 Pages.

"Microsoft Accelerates Industry Cloud Strategy for Healthcare with the Acquisition of Nuance", Retrieved From: https://news.microsoft.com/2021/04/12/microsoft-accelerates-industry-cloud-strategy-for-healthcare-with-the-acquisition-of-nuance/, Apr. 12, 2021, 9 Pages.

"Microsoft Cloud for Healthcare", Retrieved From: https://web.archive.org/web/20210706155859if_/https://www.microsoft.com/en-US/industry/health/microsoft-cloud-for-healthcare, Jul. 6, 2021, 7 Pages.

Alkasab, Tarik, "Moving Beyond Words: Artificial Intelligence and the Transformation of Radiology", In the White Paper of Healthcare Solutions, Dec. 2017, 4 Pages.

Biswal, et al., "CLARA: Clinical Report Auto-Completion", In Repository of arXiv:2002.11701v2, Mar. 4, 2020, 12 Pages.

Brady, Adrian P., "Error and Discrepancy in Radiology: Inevitable or Avoidable?", In Journal of Insights into Imaging, vol. 8, Issue 1, Dec. 7, 2016, pp. 171-182.

Gómez, Raúl, "Understanding Ranking Loss, Contrastive Loss, Margin Loss, Triplet Loss, Hinge Loss and All those Confusing Names", Retrieved From: https://gombru.github.io/2019/04/03/ranking_loss/, Apr. 3, 2019, 16 Pages.

Chen, et al., "A Simple Framework for Contrastive Learning of Visual Representations", In Proceedings of the 37th International Conference on Machine Learning, Jul. 13, 2020, 11 Pages.

Chen, et al., "UNITER: UNiversal Image-TExt Representation Learning", In Proceedings of 16th European Conference on Computer Vision, Aug. 23, 2020, 17 Pages.

Gutmann, et al., "Noise-Contrastive Estimation: A New Estimation Principle for Unnormalized Statistical Models", In Proceedings of the 13th International Conference on Artificial Intelligence and Statistics, May 13, 2010, pp. 297-304.

Hosny, et al., "Artificial Intelligence in Radiology", In Journal of Nature Reviews Cancer, vol. 18, Issue 8, Aug. 2018, 27 Pages.

Kim, et al., "ViLT: Vision-and-Language Transformer Without Convolution or Region Supervision", In Repository of arXiv:2102.03334v2, Jun. 10, 2021, 12 Pages.

Liao, et al., "Multimodal Representation Learning via Maximization of Local Mutual Information", In Repository of arXiv:2103.04537v1, Mar. 8, 2021, 10 Pages.

Sevenster, et al., "Algorithmic and User Study of an Autocompletion Algorithm on a Large Medical Vocabulary", In Journal of Biomedical Informatics, vol. 45, Issue 1, Feb. 2012, pp. 107-119.

Shad, et al., "Medical Imaging and Machine Learning", In Repository of arXiv:2103.01938, Mar. 2, 2021, 9 Pages.

Wallace, Simon, "98% of Clinicians Say They've Experienced Burnout Feelings. But How Would They Prevent it?", Retrieved From: https://whatsnext.nuance.com/healthcare/overload-to-burnout-himss/, Apr. 20, 2021, 3 Pages.

Weng, Lilian, "Contrastive Representation Learning", Retrieved From: https://lilianweng.github.io/lil-log/2021/05/31/contrastive-representation-learning.html, May 31, 2021, 33 Pages.

"Interactive. Image-rich. Insightful", Retrieved From: https://www.philips.com/c-dam/b2bhc/master/landing-pages/carestream/enterprise-imaging-platform/brochures/PHCIS_Brochure_05-Interactive_Multimedia_Reporting.pdf, Sep. 2019, 6 Pages.

Folio, et al., "Multimedia-enhanced Radiology Reports: Concept, Components, and Challenges", In Journal of RadioGraphics, vol. 38, Issue 2, Mar. 12, 2018, pp. 462-482.

Kumar, et al., "What is Microsoft Cloud for Healthcare?", Retrieved From: https://docs.microsoft.com/en-US/industry/healthcare/overview, Oct. 28, 2020, 6 Pages.

"Explosion of AI in Healthcare: Why Medtech-IT Collaborations are Key to Success", In White Paper of Frost & Sullivan, 2021, 12 Pages.

"FDA Clears 'Instant Triage' Radiology Algorithm for Pneumothorax", Retrieved from: https://www.med-technews.com/news/fda-clears-instant-triage-radiology-algorithm/, Mar. 13, 2020, 2 Pages.

"Google Launches AI Health Tool for Skin Conditions", Retrieved from: https://www.ft.com/content/6d4cd446-2243-43f4-befd-565b4e880811, May 18, 2021, 3 Pages.

Tang, et al., "Automated Abnormality Classification of Chest Radiographs using Deep Convolutional Neural Networks", In Journal of NPJ Digital Medicine, vol. 3, Issue 1, May 14, 2020, 8 Pages.

Salmon, et al., "A Review On Utilizing Machine Learning Technology in The Fields of Electronic Emergency Triage and Patient Priority Systems in Telemedicine: Coherent Taxonomy, Motivations, Open Research Challenges and Recommendations for Intelligent Future Work", In Journal of Computer Methods and Programs in Biomedicine, vol. 209, Sep. 1, 2021, 54 Pages.

"NHS Backlog Data Analysis", Retrieved from: https://web.archive.org/web/20220130062741/https:/www.bma.org.uk/advice-and-support/nhs-delivery-and-workforce/pressures/nhs-backlog-data analysis, Jan. 30, 2022, 9 Pages.

"Screening and Earlier Diagnosis", Retrieved from: https://web.archive.org/web/20210716141546/https:/www.england.hhs.uk/cancer/early-diagnosis/screening-and-earlier-diagnosis/, Jul. 16, 2021, 4 Pages.

"Standards for Interpretation and Reporting of Imaging Investigations, Second Edition", Retrieved from: https://www.cr.ac.uk/system/

(56) References Cited

OTHER PUBLICATIONS files/publication/field_publication_files/bfcr181_standards_for_interpretation_reporting.pdf, Mar. 2018, 17 Pages.

Baker, Ted, "A National Review of Radiology Reporting within the NHS in England", In Publication of Care Quality Commission, Jul. 18, 2018, 26 Pages.

Spiritoso, et al., "Chest X-Ray Interpretation in UK Intensive Care Units: A Survey 2014", In Journal of the Intensive Care Society, vol. 16, Issue 4, May 18, 2015, pp. 339-344.

Borowiec, Steven, "AI and X-Rays: Identifying the many Faces of COVID-19", Retrieved from: https://news.microsoft.com/apac/features/ai-and-x-rays-identifying-the-many-faces-of-covid-19/, Mar. 16, 2021, 7 Pages.

Froehle, Craig, "Improving Care and Efficiency through Analytics: Automating Patient Triage in Radiology", In Article of University of Cincinnati, Sep. 16, 2013, 42 Pages.

Gargeya, et al., "Automated Identification of Diabetic Retinopathy Using Deep Learning", In Journal of Ophthalmology, vol. 124, Issue 7, Jul. 2017, pp. 962-969.

Hao, Karen, "Doctors are Using AI to Triage Covid-19 Patients. The Tools may be here to Stay", Retrieved from: https://www.technologyreview.com/2020/04/23/1000410/ai-triage-covid-19-patients-health-care/, Apr. 23, 2020, 11 Pages.

Harris, Simon, "The Benefits of Comprehensive AI Solutions for Medical Imaging", In White Paper of Signify Research, Feb. 2021, pp. 1-10.

Huang, et al., "Fusion of Medical Imaging and Electronic Health Records using Deep Learning: A Systematic Review and Implementation Guidelines", In Journal of NPJ Digital Medicine, vol. 3, Issue 1, Oct. 16, 2020, 9 Pages.

Joshi, et al., "Artificial Intelligence: How to Get it Right", Retrieved from: https://www.nhsx.nhs.uk/media/documents/NHSX_AI_report.pdf, Oct. 2019, 55 Pages.

\* cited by examiner

GENERATING REPORTS FROM SCANNED IMAGES

BACKGROUND

A condition of a human or animal subject (e.g. patient) is often estimated at least in part based on one or more bodily scans, which produce images of the subject's body using imaging technologies such as x-ray, positron emission tomography (PET), magnetic resonance imaging (MRI), ultrasound or microscopy. For example such scans could be used to diagnose an illness of the subject, such as cancer.

Conventionally, a human practitioner (e.g. radiologist) reviews the one or more scans and then manually writes a report giving his or her assessment of the scans. This may include for example a possible diagnosis of one or more conditions which the scan may reveal, and a written explanation of which features in the scan are indicative of the possible diagnosis. For example a radiologist reviewing a chest x-ray might write "A mass is present in the left lower lobe and therefore malignancy must be considered".

More recently machine learning (ML) has been applied to try to improve the quality of such reports. Machine learning is a form of artificial intelligence (AI) which learns to produce a desired output based on training data, using either a supervised, reinforcement or unsupervised approach. For example a common form of ML model is a neural network.

There are two existing approaches to applying machine learning in medical reporting.

In the first approach, the process begins with the machine learning model. Before the user has reviewed the scanned images, the machine learning model receives the scanned images as an input and autonomously generates and initial draft report. Only then does the human practitioner (e.g. radiologist) manually review the image(s) and review the automated report against his/her own examination of the image(s). The human practitioner then amends the report accordingly based on his/her own professional judgment.

In the second, alternative approach, the process begins with the human practitioner. Before the machine learning model is involved, the human practitioner manually reviews the images(s) and manually writes the report from scratch based on his/her own professional judgment. After that, the text of the report is input into a machine learning model to automatically review the report. In this case the machine learning model does not analyse the images, and only reviews the report for format, style or terminology, to try to achieve a degree of standardization across the reports of different practitioners.

SUMMARY

It is recognized herein that both the approaches are limited, and neither allows for any interactivity between the user (practitioner) and the machine learning model.

According to one aspect disclosed herein, there is provided a computer implemented method comprising: receiving a current report on a condition of a human or animal subject, the current report comprising text composed by a user based on examining one or more scans of the subject (each of the one or more scans comprising at least one image of at least part of the subject); receiving the one or more scans; and inputting the current report and the one or more scans into a trained machine learning model. The machine learning model is pre-trained based on a plurality of past scans and corresponding reports composed based on the past scans (the past scans comprising at least some scans of other subjects). Based on the current report and the one or more scans of the subject, the machine learning model generates one or more suggestions for updating the text of the current report. The method further comprises and outputs data to cause a user interface to display to the user one or more suggestions for updating the text of the report, with each respective suggestion visually linked in the user interface to a corresponding subregion within at least one image of at least one of the one or more scans based upon which the respective suggestion was generated.

Thus by inputting both images and reports into the model, the disclosed method provides for a "feedback loop" between the human user and the model: the human begins by writing the report based on his/her expertise, and then the model reviews both the image(s) and the report together in order to provide suggestions back to the user for potentially updating the report, if he/she sees fit based on his/her professional judgment. Furthermore the user interface provides a visible link between the suggestions and the cause of the suggestions in the image(s), e.g. by highlighting areas of the image in the same colour as the suggestions, thus enabling the user to better assess the suggestions made by the model. The disclosed method thus provides a true "assisted AI" approach to the review of medical scans and the like.

In embodiments, the method may comprise receiving back at least one update to the current report entered by the user through the user interface based on at least one of the one or more suggestions, and updating the current report with the at least one update to produce an updated report. The one or more updates may comprise acceptance by the user of one or more of the suggestions made by the model, and/or one or more alternative amendments composed by the user.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Nor is the claimed subject matter limited to implementations that solve any or all of the disadvantages noted herein.

BRIEF DESCRIPTION OF THE DRAWINGS

To assist understanding of the present disclosure and to show how embodiments may be put into effect, reference is made by way of example to the accompanying drawings in which.

DETAILED DESCRIPTION OF EMBODIMENTS

Figure 1:
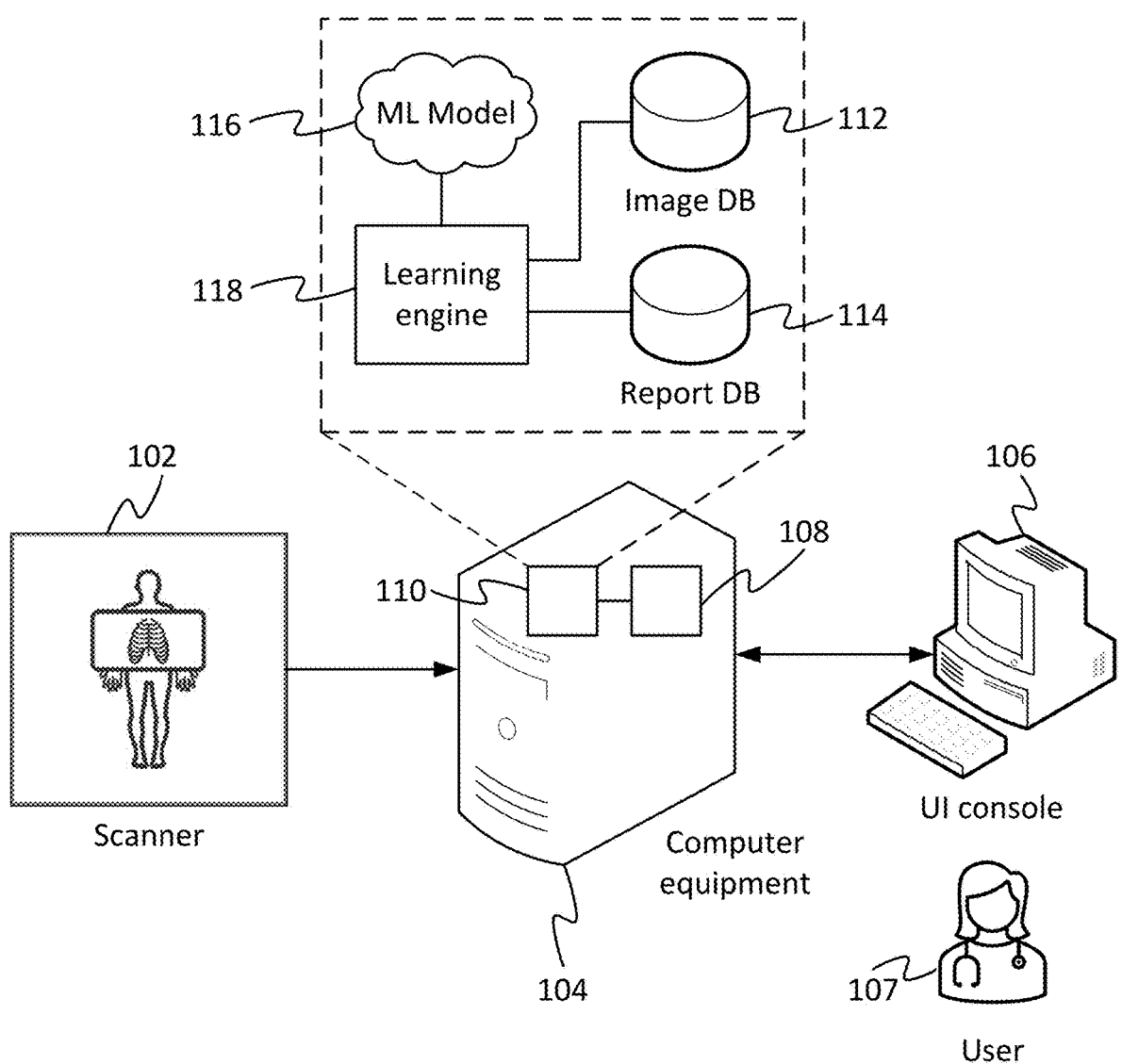
FIG. 1 is a schematic block diagram of a system for scanning subjects and generating reports in accordance with embodiments disclosed herein.

According to one estimate, on average 3-5% of reports in the USA contain misinformation and inconsistencies in radiological findings. Similar issues may be encountered in other territories and other fields of diagnosis. This creates a desire for safety-nets in reporting and its systematic review before they are shared with patients or colleagues. In such clinical workflows, machine learning (ML) models could own a complementary role by providing a second opinion at the time of diagnosis and reporting. In this way, potential oversights may be identified and misdiagnosis rates can be reduced whilst ensuring standardisation and completeness of radiological reporting. Additionally, this can save time, improve productivity, and enhance report quality and consistency.

The present disclosure provides a user interface (UI) for a radiology workflow, or the like, that is assisted by AI. The AI is trained on both images and reports, such that in use the AI parses image and report data in an online manner and provides real-time feedback to the user (e.g. radiologist) to ease the task of reporting and enhance the quality of output radiological reports, or the like. The suggested content is highlighted in the scan, e.g. in yellow, and this can then either be accepted or rejected by the user. In case of doubt, the user can verify the suggested content in the image by cross-checking against the highlighted region in the image (e.g. radiograph). Potential errors in the human generated report can thus be identified by the AI but checked by the user, in a feedback loop which provides the user with suggestions while writing the report in an ongoing manner. In embodiments, the user is able to highlight an area of the image in order to determine the diagnosis that relates to that region. Similarly the user can highlight the text to identify the corresponding region on the image. The identification of incorrect associations by the machine may be used to improve the model. I.e., the user's feedback can be used to refine the training of the model in an ongoing manner.

Other ML technologies have been developed by commercial entities aiming to fully automate the radiological reporting process by analyzing chest radiographs with machine learning models. The presently disclosed approach differs from such prior work by its user-interactive nature that involves a user-interface and feedback loop between the user and machine. It places clinicians at the centre of the process and focuses on empowering them through its rich and assistive user-interface. It provides real-time feedback to users on any missing or inaccurate content whilst offering suggestions, e.g. leading to the use of common terminology. Further, the disclosed approach links each suggested report content with the corresponding anatomical region seen in radiological scans, or the like. It can thus reassure the user that the system has a good understanding of the data, or in case of a disagreement such additional information can avoid any confusion on why the model made this suggestion. This technology could find other beneficial applications in areas such as digital pathology. For instance, biopsy findings can be documented in a more structured and assisted manner in clinical forms through use of machine learning tools. This includes information relating to location, tissue staining, tumor severity, tumor type and pathologists' observations made in diagnosis, for example.

FIG. 1 shows a system in accordance with embodiments of the present disclosure. The system comprises at least one scanner 102, computer equipment 104, and at least one user interface (UI) console 106. The at least one scanner 102 and the UI console 106 are operatively coupled to the computer equipment 104, either directly or via one or more networks, such as the Internet, a mobile cellular network, and/or a private wired or wireless intranet of an organization (e.g. hospital, health organization or research institute). It will be appreciated that any data, signals or information described below as being exchanged between scanner 102 and computer equipment 104, and between computer equipment 104 and UI console 106, may be conducted by any such means of connection and/or others.

The at least one scanner 102 comprises a scanner for producing scans of at least a bodily part of a human or animal subject, living or dead, based on one or more scanning media types. For example the at least one scanner 102 may comprise an x-ray based scanner for producing x-ray scans, a PET scanner for producing PET scans, an MRI scanner for producing MRI scans, an ultrasound scanner for producing ultrasound scans, and/or scanning electron microscopy equipment for producing electron microscopy based scans. Another example could be visible light photography equipment for producing scans in the form of photographs. In embodiments the system may comprise multiple types of scanner for producing multiple types of scan of a given subject based on different scanning media (e.g. x-ray and MRI, x-ray and PET, PET and MRI, etc.). Alternatively only a single scanner employing a single type of scanning medium may be used, e.g. x-ray only, or MRI only, etc. Note also that for a given scanning medium type, there may be different options from producing an image. For example an x-ray based scan as referred to herein could refer to an x-ray photograph or a more sophisticated form of scan based on x-rays as the probing medium, such as a CT (computed tomography) scan. Or a visible light based scan could refer to a simple macroscopic visible light photograph or an optical microscopy based scan.

Each individual scan may comprise one or more images. In the case of multiple images per scan, the scan may for example comprise a 3D "stack" of 2D images ("slices"), each image comprising a cross-section through the subject taken at a different respective depth. For instance, while a simple x-ray photograph may comprise only a single x-ray image, a more sophisticated x-ray technology such as a CT (computed tomography) scan may comprise a stack of images representing slices through the subject at different depths, thus creating a tack of 2D images representing a 3D volume of at least a portion of the subject's body. The scanning equipment 102 may be used to take a 2D or 3D scan of a given subject on a single occasion or multiple such scans taken on multiple different respective occasions (different times), e.g. spaced apart by hours, days, weeks, months or years.

The computer equipment 104 may comprise a single computer unit in a single housing, or multiple units in separate housings at one or more sites and networked together using any suitable network technology. For example the computer equipment 104 may comprise one or more server units. E.g. the computer equipment 104 may comprise multiple server units in the same rack, or different units or racks in the same room, different units or racks in different rooms of the same facility or data centre, and/or different facilities or data centres at different geographic sites. In the case of multiple computer units (e.g. server units), these may for example be networked together via a server area network, local area network, intranet, campus area network, metropolitan area network and/or a wide-area network or internetwork such as a mobile cellular network and/or the internet.

The UI console 106 may be integrated into one or more of the computer units of the computer equipment 104, and/or may comprise one or more separate computer terminals or dedicated UI peripherals. The UI console 106 comprises at least one display screen, and at least one form of user input means (e.g. a touch screen and/or point-and click interface of the display, and/or a keyboard or voice interface). The UI console is thus able to provide a user interface (UI) for outputting the images of the scans to a user 107, receiving text from the user 107 for writing reports based on the images, and displaying the text of the reports and associated suggestions generated by the computer equipment 104 based on the original text and image(s). The user 107 may comprise for example a medical practitioner, veterinarian, or a researcher. The user 107 may comprise a single such person or a team of two or more people.

The computer equipment comprises processing apparatus 108 comprising one or more processors, and memory 110 comprising one or more memory units. The processor, or each processor, may take any suitable form such as a CPU (central processing unit), or a dedicated AI accelerator processor, or some other, re-purposed form of application-specific processor such as a GPU (graphics processing unit), crypto-processor or DSP (digital signal processor). The memory unit, or each memory unit, may take any suitable form, e.g. an electronic memory medium such as a SSD (solid state drive), flash memory, ROM (read only memory), EEPROM (electrically erasable and programmable ROM), RAM (random access memory), SRAM (static RAM), and/or DRAM (dynamic RAM); and/or a magnetic memory such as a hard drive, removable magnetic disk, and/or magnetic tape drive; and/or optical memory such as CD (compact disc), DVD (digital versatile disk), other magnetic disk, quartz glass storage, and/or magneto-optical drive; and/or synthetic biological storage such as synthetic DNA storage.

Whatever form it takes, the memory 110 is arranged to store an image database 112, a report database 114, a machine learning model 116, and a learning engine 118. The image database stores the image data from one or more scans taken by the at least one scanner 102. It may also store one or more past or historic scans which may have been taken via the same scanning equipment 102 or other scanners, or a combination. The report database 114 stores a report authored by the user 107 via the UI console 106. It may also store one or more past or historic reports authored based on the past or historic scans, which may have been authored via the UI of the same UI console 106 or a different UI, by the same user 107 or a different user, or a combination.

The machine learning model 116 may comprise one or more neural networks, or any other form of statistical model capable of learning based on training data, such as a clustering model. The machine learning engine 118 comprises software arranged to take one or more scans from the image database 112 and one or more associated reports from the report database, and input them to the machine learning model 116 to cause it to make predictions (also called inferences) based on the input image and report data. Particularly, these predictions comprise one or more suggested updates to the report(s), as will be discussed in more detail shortly. The machine learning engine 118 may also comprise one or more machine learning algorithms arranged to train the machine learning model 116 based on past images and associated reports from the image database 112 and report database 114 respectively. Alternatively the model may have been trained elsewhere, on other computer equipment (not shown), and copied to the memory 110.

Figure 2:
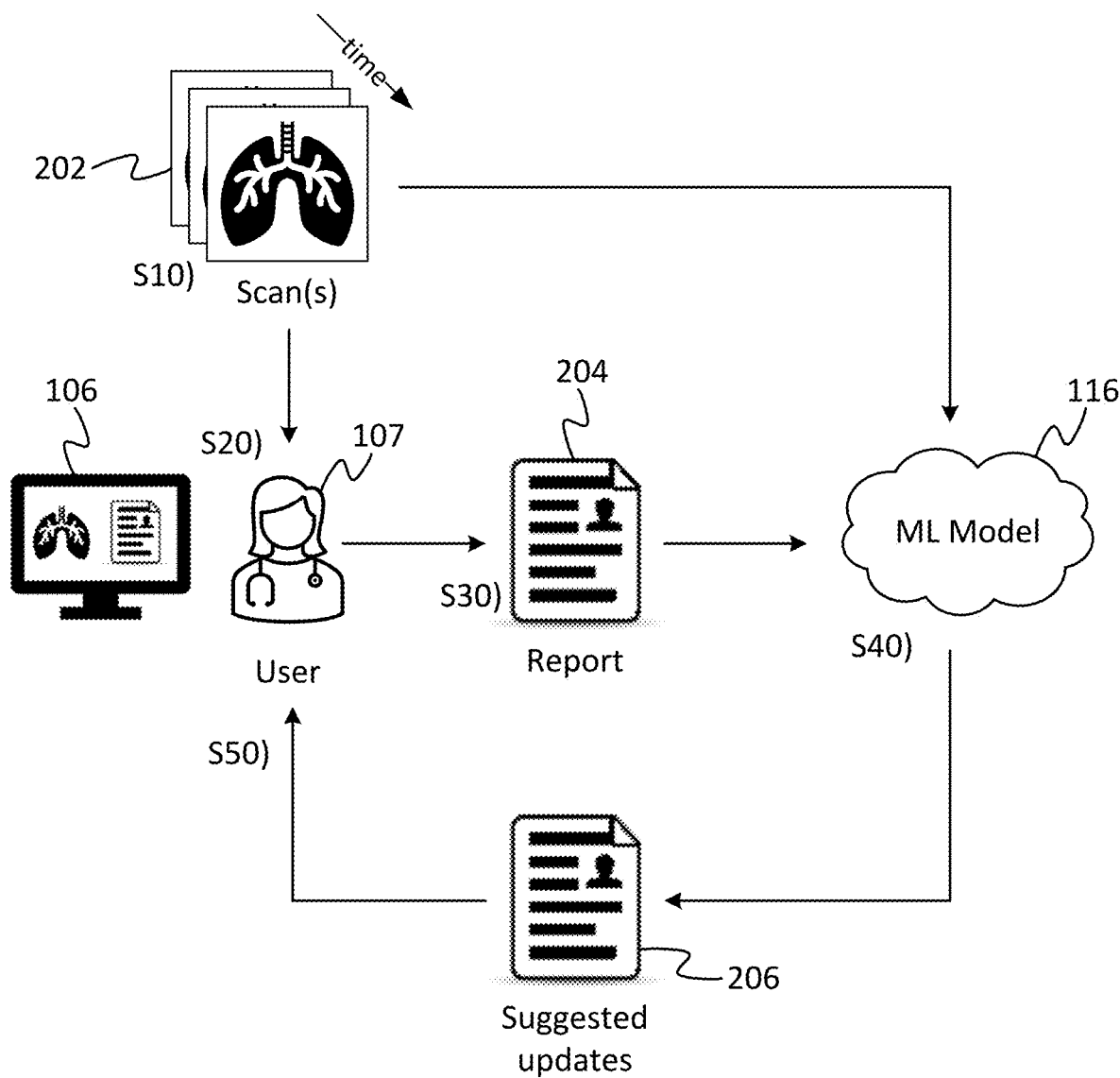
FIG. 2 is a flow chart of a method of generating reports in accordance with embodiments disclosed herein.

FIG. 2 shows a method that may be implemented using the system of FIG. 1. The method is to be used to estimate a condition (e.g. disease or cause of death) of a target subject. The target subject is either a human or an animal (e.g. mammal, bird, fish, marsupial or invertebrate).

Prior to the method there is a preliminary step of training the machine learning model 116. The model 116 is trained based on a plurality of past scans (preferably tens, hundreds, thousands or more) of one or more subjects, together with associated reports including text authored based on a review of the respective scans. The past scans preferably comprise one or more of scans at least one subject other than the target subject (but of the same species). They may also include one or more past scans of the target subject. The reports of the past scans may have been authored purely manually, or with AI assistance. They may have been authored by the same user 107 who is to author the new report on the target subject using the method of FIG. 2, or a different user, or a combination. Preferably the past reports include at least some reports authored by different users so as to introduce some variation in style into the training data. Either way, the training may comprise a supervised approach, reinforcement approach or unsupervised approach.

The machine learning model 116 is thus trained to be able to receive the image(s) of a current scan and an associated report, and to output suggestions for updating the text of the report.

At step S10) at least one current scan 202 is taken of the target subject using the at least one scanner 102. As discussed earlier this may comprise for example an x-ray based scan (e.g. CT scan), a PET scan, an MRI scan or an ultrasound scan, or a combination. Each scan 202 may comprise a single 2D image, or a 3D stack of 2D images (e.g. as set of "slices" through the subject).

At step S20), the user (e.g. radiologist, vet or researcher) 107 reviews the one or more images of the current scan 202, or each current scan, though the user interface (UI) displayed on the UI console 106.

At step S30), based on the review, the user 107 authors a draft report 204 (or at least part thereof)—at this stage using his/her professional judgment only (not AI). The report 204 comprises text written by the user 107. The text comprises a description of one or more possible conditions (e.g. diseases) which the target subject may have based on the review. The text may also include an explanation of why the user 107 came to this conclusion, e.g. what features in the image(s) led to this.

At step S40) the image data of the one or more current scans 202 are input into the machine learning model 116, together with at least the text of the corresponding report 204. Based on the report and image(s) together, the machine learning model 116 generates one or more suggestions for amendments 206 to the text of the report 204. For example the suggestions may comprise the addition of one or more potentially missing details, the correction of one or more possible errors, and/or one or more suggestions for alternative terminology (e.g. for clarity or to promote consistency across reports).

At step S50) the suggested amendments 206 are presented to the user through the UI on the UI console 106. For example they may be presented on screen in the form of a proposed updated version of the report, e.g. with the amendments shown tracked (marked-up) on the previous version of the report (such as by means of strikethrough, underlining and/or highlighting). Further the machine learning model 116 is able to identify which part of the image (or which part of which image) resulted in each suggestion. This is indicated visually to the user 107 through the UI, linking each suggestion to a particular corresponding feature in the image (or one of the images). In other words the UI indicates to the user the cause of each suggestion in the image. Some examples for this will be discussed in more detail shortly with respect to FIG. 3.

The user 107 then reviews each of the one or more suggestions made by the machine learning model 116. However the suggested amendments are not finalized autonomously by the AI. Only if the user 107 deems fit based on his/her professional judgment will he/she choose to accept each update to be included into an actual updated version of the report. The user 107 may accept the suggestions though the UI, for example by selecting to accept or reject each one individually, or selecting accept all or reject all. The selection is made through the UI on the at least one UI console 106, e.g. via a mouse, touchscreen, keyboard or voice input. As another possibility, upon being prompted to reconsider the wording by the suggestion from the machine learning model 116, the user 107 may choose to make an alternative amendment that was neither the original wording nor the suggestion from the ML model 116.

If the user 107 accepts one or more of the suggested amendments, and/or makes one or more amendments of his/her own, then optionally steps S30) to S50) may be repeated with the updated report in order to generate one or more updated suggestions. That is, the amended report (as amended in the first iteration of the method) is input into the machine learning model 116, again along with the corresponding image data of the one or more current scans. The machine learning model 116 processes these together in order to output one or more updated suggestions, which are presented to the user 107, and which the user may again accept or reject, or may make one or more further alternative amendments of his/her own, thus creating a further updated version of the report. In embodiments, the method may continue over one or more yet further iterations in a similar manner, each time the ML model 116 analysing the previously updated version of the report.

Note the method shown in FIG. 2 may be somewhat schematized compared to the actual implementation. For instance, in embodiments it is not necessary for the user 107 to compose the entire report 204 and then input it as a whole into the model 116 before the suggestions 206 can start to be generated. In embodiments, the suggestions could be generated and output to the user 107 live as he or she types the report. I.e. the suggestions are output dynamically, or "on the fly", in real-time as the user types, with one or more suggestions being generated and output to the user 107 based on the report as composed so-far before the user 107 has finished writing the whole report.

In embodiments the training of the machine learning model 116 may also be refined with each iteration of the method, i.e. based on the user accepting or rejecting the model's suggestions in each of the one or more rounds of the method.

In some scenarios, then at some point after at least one iteration of the method, one or more additional scans of the target subject may be performed. This adds new image data into the system as well as updated report data. For example, a new scan of the target subject may be performed after a matter of hours, or the next day, next week, next year or next year. The arrow labeled "time" in FIG. 2 represents the possibility of additional scans being added over time (where the different schematized icons labeled 202 in the figure represent different scans taken on different occasions). This provides one or more new images of the target subject, which may be added only after the initial report has been authored and reviewed at least once by the ML model 116. In this case, the method may comprise inputting the new image data from the one or more additional scans into the machine learning model 116, along with the latest version of the report (including any amendments accepted by the user 107). Based on these, the ML model 116 may the output one or more additional suggestions taking into account the new images. These are output to the user 107 through the UI, in order for the user to review and accept or reject them based on his/her judgment, in a similar manner as described earlier.

In embodiments, the training of the machine learning model 116 may also be refined based on the image(s) of the additional scan(s), and optionally any additional amendments which the user 107 accepts, rejects or makes him/herself based on the new scan(s).

Figure 3:
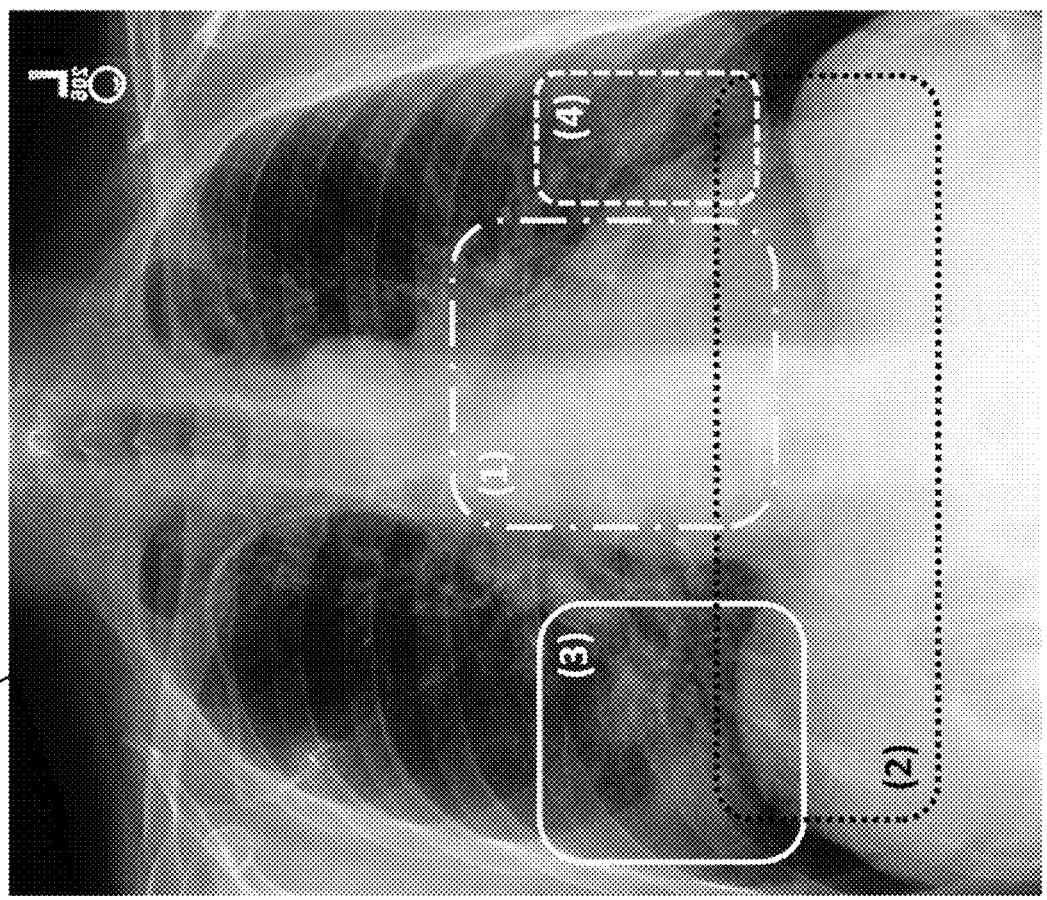
FIG. 3 is schematic mock-up of an example user interface in accordance with embodiments disclosed herein.

FIG. 3 schematically illustrates an example of the way in which suggested updates may be output to the user 107 through the UI.

An image of the scan 202, or one of the scans, is displayed to the user 107 on a screen of the UI console 106. A version of the report 204 is also displayed to the user on screen, either on the same screen or a different screen of the UI console. The version of the report includes the one or more suggested amendments shown inline in the text, in tracked (marked-up) form. E.g. this may comprise underlining, putting in bold or highlighting any additions; and/or showing any deletions in strike-through. Furthermore, the UI includes a visual effect that links each suggestion to a corresponding area within the image currently on screen (or one of the images), showing which particular part of the image caused the suggestion to be generated. By an area or region within the image, or such like, it is meant a particular are smaller than the image itself, i.e. a subregion of the image. There are a number of possible ways in which suggestions in the text and corresponding regions within an image may be linked.

For example, the UI may highlight the suggestion in a certain colour, and highlight the corresponding part of the image in substantially the same colour. If different suggestions are based on different parts of the image, the different suggestions may be highlighted in different colours, and each part of the image may be highlighted in the same colour as the particular suggestion which it generated. In the black & white mock-up of FIG. 3, different types of dotted line are used to schematically represent highlighting in different colours. However another option would indeed be to outline in different line types. A suggested amendment and corresponding image area could be highlighted by the drawing of a box or other shaped line around the text and image area and using a certain colour and/or line type for the box or line, or the highlighting could be by using a certain background colour behind the text and image area, or a tint thereover, or any combination of these effects and/or others.

In the example of FIG. 3, the UI highlights a suggestion by highlighting a whole phrase in which a suggestion is included, and within the highlighted phrase underlines the suggested amendment itself and/or shows it in bold. However this is just one example. Another would be to highlight only the suggested amendment itself.

Another alternative or additional option, as also shown in FIG. 3, is for the UI to mark each suggestion with a particular respective reference sign, such as a letter or numeral, and to mark each corresponding region in the image with the same reference sign. Another example, not shown, would be to display a line connecting the amendment or the phrase containing the amendment to the corresponding region in the image.

If the report is longer than can be shown on screen all at once, the UI may provide the user with the ability to scroll through the report or flip through different pages or sections. Also if the report 204 was based on more than one scan 202, the user 107 may have the option in the UI to flip or scroll through the different scans. If a given scan comprises more than one image (e.g. slice), the user may have the option in the UI to flip or scroll though the different images of the scan. Alternatively or additionally, the UI may automatically switch to one or more images corresponding to whatever section or page of the report the user has selected to view at the moment, or vice versa, automatically switch to the section or page of the report that corresponds to whatever image the user has selected to view at the moment. The UI will show how the suggestions on screen at the time are linked to whatever image is on screen at the time.

The amendment suggested by the ML model 116 could be to suggest some extra detail that the user 107 did not include in the original report. E.g. in phrase 3) in the example of FIG. 3, the user 107 may have omitted to add that the opacities are in the right lower lobe, so the ML model 116 suggests to add this in. In some cases the model 116 could even suggest the insertion of a whole phrase that the user did not include, e.g. as in phrase 2) in the example of FIG. 3. Another type of amendment that may be suggested by the ML model is the correction of an error or a change to some terminology in the user's original report, perhaps where the user used language that was potentially misleading, non-standard or imprecise. E.g. in phrase 1) in FIG. 3, the user may have originally written that the heart size appears "fine", but the ML model 116 may suggests to change this term to "normal" because this is more formal, more standard, and/or more informative or precise. In some embodiments, the UI could also show how any phrases that the ML model 116 agreed with (had no suggestions for) map to a part of the image. E.g. see phrase 4) in FIG. 3. This may give reassurance that the model has still considered this part of the report and shows the part of the image that led the model to agree with the user.

In some embodiments, the UI may enable the user 107 to select a particular suggestion, such as by clicking on, hovering over or touching the suggestion or a phrase containing the suggestion. In response, the UI will emphasize the corresponding region within the image, such as by making the highlighting more intense compared to the other highlighted parts of the image, or causing it to flash. Alternatively or additionally, the UI may enable the user 107 to select a particular highlighted region of the image (or one of the images), such as by clicking on, hovering over or touching the region. In response, the UI will emphasize the corresponding suggestion within the marked-up report, e.g. again by making the highlighting more intense compared to the other highlighted suggestions in the text of the report, or making it flash, etc.

In further alternative or additional embodiments, the machine learning model 116 may also be used to review historical report data. In this case the machine learning model 116 is arranged to search through a plurality of past reports and the associated scans based upon which the reports were originally authored. Based on both the text of the reports and the associated images, the machine learning model 116 may then identify one or more of the historical reports that contains a possible error.

The ability to perform machine learning based on multiple modalities, such as both images and text, is in itself known in the art. This includes the ability to correlate predictions in the text with causes in an image. See for example "A simple Framework for Contrastive Learning of Visual Representations", Ting Chen et al.

Figure 4:
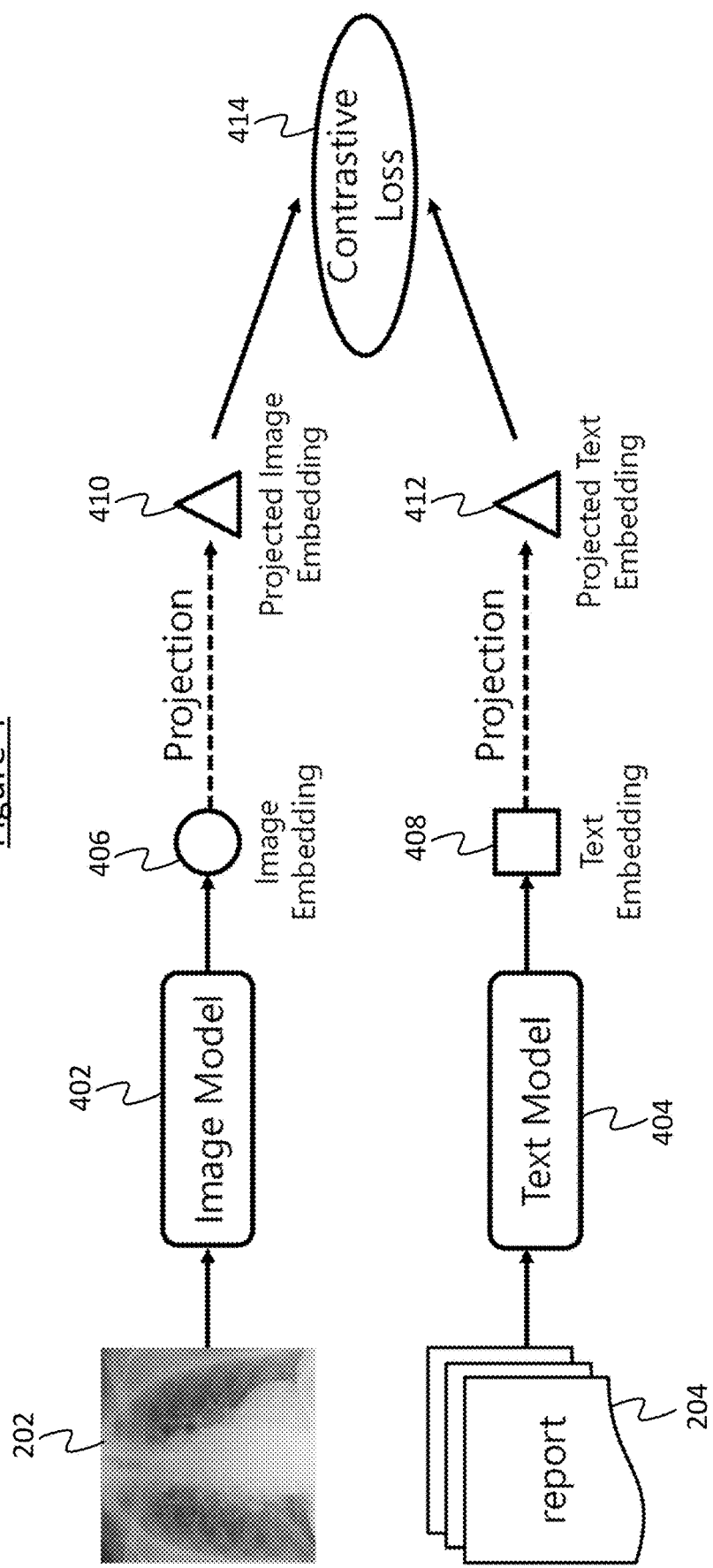
FIG. 4 is a schematic representation of a machine learning model in a training phase in accordance with embodiments disclosed herein.
Figure 5:
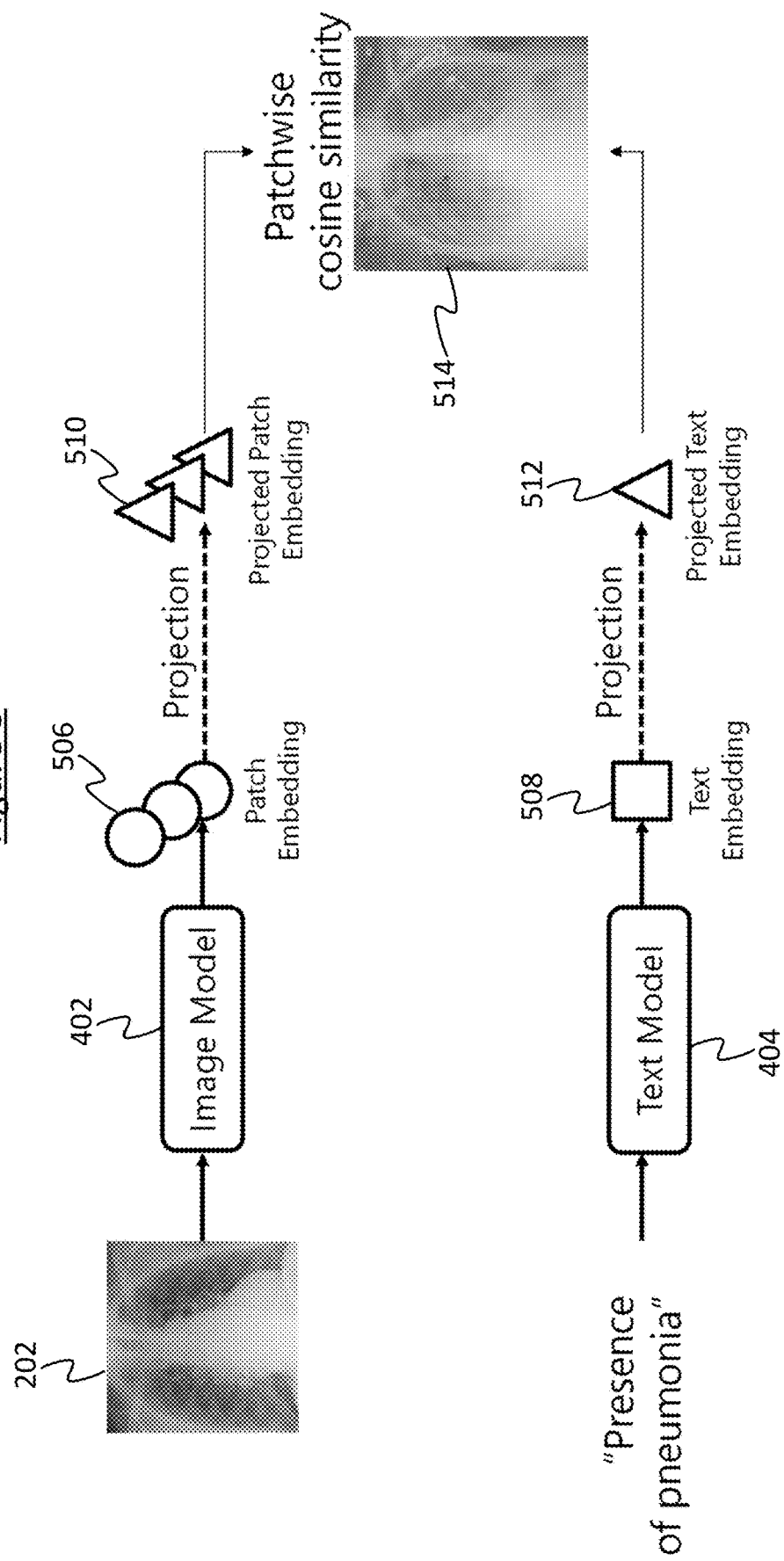
FIG. 5 is a schematic representation of a machine learning model in a deployment phase in accordance with embodiments disclosed herein.

FIGS. 4 and 5 show an example of how the machine learning model 116 may be implemented in embodiments of the present disclosure. FIG. 4 shows the model 116 in the learning phase (when being trained) and FIG. 5 shows the model 116 in the deployment phase (when being used to review reports 204 and generate suggestions 206).

As shown in FIG. 4, the ML model 116 comprises an image model 402 arranged to receive the image data of one or more scans 202 as an input, and a text model 404 arranged to receive the text of the corresponding report 204 as an input. In the learning (training) phase, the image model 402 outputs an image embedding 406 based on the input image data, and the text model 404 model outputs a text embedding 408 based on the input text. A projection of the image embedding 406 is performed to generate a projected image embedding 410. A projection of the text embedding 408 is performed to generate a projected text embedding 412. The projected image embedding 410 and projected text embedding 412 are then input into an alignment stage 414 such as a contrastive loss stage.

An embedding is a representation of the information from the input vector in compressed, numerical form. This is also sometimes referred to as a "latent vector". The image model 402 learns to encode the images from the scans 202 into the image embedding 406, and the text model learns to encode the text from the reports 204 into the text embedding 408. The image embedding captures a kind of "summary" of the visually relevant information content in the image data, and the text embedding captures the semantically relevant information in the text. The concept of an embedding or latent vector will, in itself, be familiar to a person skilled in the art. Each of the image model 402 and the text model 404 may take the form of a neural network arranged as an encoder network. Encoders for encoding image and text data into latent space are, in themselves, known in the art.

A projection converts an embedding into another embedding for the purpose of "alignment", i.e. combining between different modalities (in this case images and text). So the image embedding 406 is converted into a projected image embedding 410, and the text embedding is converted into a projected text embedding 412. The embedding 406, 408 output by each model 402, 404 (respectively) is optimized for compression, whilst the projected embeddings 410, 412 are optimized for alignment, i.e. aligning between different modalities (in this case images and text). The projection operation bridges between the two latent spaces. It converts the embedding 406/408 to a different latent space 410/412 in order to decouple alignment from compression. The projected embeddings 410, 412 are input into an alignment function 414 such as a contrastive loss function.

The alignment function 414 is a multi-modal learning function which determines a multi-modal metric that is learnt at training time. Alternatives to a contrastive loss function include margin based loss functions, and ranking based loss functions. Multi-modal learning, in itself, is known in the art. See for example "Understanding Ranking Loss, Contrastive Loss, Margin Loss, Triplet Loss, Hinge Loss and all those confusing names", Raúl Gómez, 3 Apr. 2019 (https://gombru.github.io/2019/04/03/ranking_loss/).

Based on this, the model 116 learns to project each of the image and text embeddings 406, 408 into a respective projected embedding 410, 412 which is optimized to align between the two modalities. The concept of projecting an embedding for the purpose of alignment between modalities in machine learning is, in itself, known in the art. Such a technique is described for example in Chen et al, cited above.

An advantage of learning to encode an input vector into a first embedding 406/408 optimized for compression, which is then projected into a projected embedding for alignment 410/412, is that the image model 402 and/or text model 404 can initially be trained independently of one another based on only image and/or text data (respectively). That is, the image model 402 may be part trained based on images that have no corresponding report, and/or the text model 404 may be part trained based on report data for which no corresponding images have been kept. The models 402, 406 can then be combined via the projected embeddings 410, 412 and alignment function 414 and further trained based on combined image and report data (reports for which the respective image data is still available). However, this is not essential and in other embodiments the image model 402 and/or text model 404 may be configured to encode directly into a respective embedding 410, 412 optimized for alignment. In that case the contrastive loss function 414 is replaced with a binary contrast estimation.

Other possible approaches to multi-modal machine learning include noise contrastive estimation and image-text matching loss as used in application papers. See for example
"Contrastive Representation Learning", Lilian Weng, 31 May 2021 (https://lilianweng.github.io/lil-log/2021/05/31/contrastive-representation-learning.html);
"Noise-contrastive estimation: A new estimation principle for unnormalized statistical models", Michael Gutmann et al;
"UNITER: UNiversal Image-TExt Representation Learning", Yen-Chun Chen et al;
"ViLT: Vision-and-Language Transformer Without Convolution or Region Supervision", Wonjae Kim et al.

Whatever form the ML model 116 takes, the learning engine 118 may manage the input of training data into the model 116. Over many training data samples, the learning engine 118 trains the model 116 by tuning the parameters (e.g. weights) of the model 116 based on the output, e.g. by a stochastic gradient descent algorithm. Details of how to train a machine learning model based on back propagation or the like will, in themselves, be familiar to a person skilled in the art.

FIG. 5 shows an example of how the machine learning model 116 may be used to generated suggestions in accordance with embodiments of the present disclosure. The arrangement is similar or FIG. 4, except that the image model 402 outputs a patch embedding 506, and the text model 402 may output a text embedding 508 for individual portions of text. A projection of the patch embedding 506 is performed to generate a projected patch embedding 510. A projection of the text embedding 508 is performed to generate a projected text embedding 512. The projected patch embedding 510 from the image branch of the model and the projected text embedding 512 from the text branch of the model are combined in a comparison stage 514 such as a patchwise cosine similarity stage.

In the deployment stage, the image model 402 may be applied to individual "patches" of the image 202, e.g. blocks of 16×16 pixels, and thus generate an individual patch embedding 506 and projected patch embedding 510 for each patch. Similarly the text model 404 may be applied to portions of text from the report 204, such as individual sentences, and thus generate an individual text embedding 510 and projected text embedding 512 for each portion of text.

Based on this arrangement, the learning engine 118 systematically compares a plurality of patches in the (or each) image of a given scan 202 with one or more different portions of text in the corresponding report 204 (the version of the text including any suggestions made by the ML model 116 in the current iteration). For instance the image may be divided into a grid of patches, e.g. 12×12 or 16×16 squares, and for a given portion of text (e.g. sentence) each patch in the grid may be compared against that portion of text. In another example, a hierarchy of patch sizes could be used, e.g. the search may be performed based on a coarse grid of 16×16 pixel patches, then a finer grid of 8×8 pixel patches, etc. In yet another example, a patch of a certain size may be swept systematically across the image area. For instance a block of certain size (e.g. 16×16 pixels) may start in one corner of the image, then be shifted across horizontally in steps by a certain delta (e.g. 4 pixels per shift), then shift down by one step (e.g. again 4 pixels) each time a row is complete (or mutatis mutandis sweeping vertically first and then across in columns). Another option would be a binary search. The granularity or thoroughness of the search is only limited by the computational resources of the computing equipment used.

For each patch that is compared with each portion of text (i.e. for each possible pairing between one patch and one text portion in the search), the projected patch embedding 510 for the image patch in question is input into the comparison function 514 along with the projected text embedding 512 for the portion of text currently being analysed. The comparison function, e.g. patchwise cosine similarity function, outputs an indication of an estimated similarity or likelihood of a match or correlation for the compared imaged patch and text portion. This may then be thresholded to determine whether to indicate that patch as mapped to the text portion in the UI.

Cosine similarity is the most common metric to measure the similarity between a pair of projections. However, more generally the comparison function 514 could be any other similarity metric such as mean-squared error.

It will be appreciated that the above embodiments have been disclosed by way of example only.

More generally, according to one aspect disclosed herein, there is provided a computer implemented method comprising: receiving a current report on a condition of a human or animal subject, the current report comprising text composed by a user based on examining one or more scans of the subject, each of the one or more scans comprising at least one image of at least part of the subject; receiving the one or more scans; and inputting the current report and the one or more scans into a trained machine learning model, the machine learning model being pre-trained based on a plurality of past scans and corresponding reports composed based on the past scans, the past scans comprising at least some scans of other subjects. Based on the current report and the one or more scans of the subject, the machine learning model generates one or more suggestions for updating the text of the current report. The method further comprises and outputs data to cause a user interface to display to the user one or more suggestions for updating the text of the report, with each respective suggestion visually linked in the user interface to a corresponding subregion within at least one image of at least one of the one or more scans based upon which the respective suggestion was generated.

In embodiments, the method may comprises receiving back at least one update to the current report entered by the user through the user interface based on at least one of the one or more suggestions, and updating the current report with the at least one update to produce an updated report. The update may comprise the user accepting one of the suggestions made by the machine learning model, or it may comprise an alternative amendment composed by the user once prompted by one of the suggestions.

In embodiments, the method may further comprise inputting the updated report into the machine model to generate one or more updated suggestions, and outputting data to cause the user interface to display the one or more updated suggestions to the user, each visually linked to a subregion within at least one image in at least one of the one or more scans based upon which the updated suggestion was generated.

In embodiments, the method may further comprise receiving back at least one further update to the report entered by the user through the user interface based on at least one of the one or more further suggestions, and further updating the updated report with the at least one further update. The further update may comprise acceptance by the user of one of the updated suggestions made by the model, or an alternative amendment composed by the user once prompted by one of the updated suggestions.

In embodiments, the method may further comprise refining the training of the machine learning model based on the at least one update and/or further update.

In embodiment, the method may further comprise: receiving one or more additional scans of the subject, taken after said one or more scans; receiving a modified version of the current or updated report having been modified by the user based on examining the one or more additional scans; inputting the one or more additional scans and modified report to the machine learning model to generate one or more modified suggestions for updating the modified report; and outputting data to cause the user interface to display the one or more modified suggestions to the user, each visually linked to a subregion within at least one image in at least one of the one or more additional scans based upon which the modified suggestion was generated.

In embodiments the method may further comprise: receiving back at least one additional update to the current report entered by the user through the user interface based on at least one of the one or more modified suggestions, and updating the current or updated report with the at least one additional update. The additional update may comprise acceptance by the user of one of the modified updates made by the machine learning model, or an alternative amendment composed by the user once prompted by one of the modified updates.

In embodiments, the method may further comprise refining the training the machine learning model based on the at least one additional update.

In embodiments, the displaying of the one or more suggestions may comprise displaying a marked-up version of at least some of the text of the current report with the one or more suggestions shown in-line.

In embodiments, the visual linkage may comprise displaying each of the one or more suggestions in association with a respective colour, and marking the corresponding subregion with substantially the same colour. For instance, the displaying of each of the one or more suggestions in association with a respective colour may comprise: displaying the suggestion using text of the respective colour, highlighting the suggestion with the respective colour, or drawing a line around the suggestion. And/or, the marking of each subregion may comprise: highlighting the subregion with the respective colour, or drawing a line of the respective colour around the subregion.

In embodiments, the visual linking may comprise displaying a respective reference sign in association with each of the one or more suggestions, and displaying substantially the same reference sign in association with the corresponding subregion.

In embodiments, the generating and displaying of the one or more suggestions may comprise generating and displaying at least one of the suggestions live as the user composes the report.

In embodiments, each of the scans may comprise one of: an x-ray based scan, a PET scan, an MRI scan, or an ultrasound scan. E.g. an x-ray-based scan may comprise a CT scan.

In embodiments, at least one of the scans may comprise a 3D scan comprising a stack of 2D images showing different cross-sectional slices through the part of the subject.

In embodiments, the user interface may enable the user to select one of the suggestions and in response indicates the subregion of the image based upon which the selected suggestion was generated. Alternatively, the user interface may enable the user to select one of the subregions in one of the images and in response indicates the suggestion in the report generated based on the selected subregion.

In embodiments, the method may further comprise applying the machine learning model to review a historical scan of the subject or another subject, together with a corresponding historical report authored based on the historical scan, to identify one or more possible errors in the historical report.

In embodiments the machine learning model may comprise one or more neural networks.

According to another aspect there is provided a computer program embodied on non-transitory computer-readable storage, configured so as when run on one or more processors to perform the method of any embodiment disclosed herein.

According to another aspect there is provided a computer system comprising: processing apparatus comprising one or more processors; and memory comprising one or more memory units, the memory storing code arranged to run on the processing apparatus, wherein the code is configured so as when run on the processing apparatus to perform the operations of any embodiment disclosed herein.

Other variants or use cases may become apparent to a person skilled in the art once given the disclosure herein. The scope of the present disclosure is not limited by the above-described embodiments, but only by the accompanying claims.

The invention claimed is:

1. A computer implemented method comprising:
   receiving a current report on a condition of a human or animal subject, the current report comprising text composed by a user based on examining one or more scans of the subject, each of the one or more scans comprising at least one image of at least part of the subject;
   receiving the one or more scans;
   inputting the current report and the one or more scans into a trained machine learning model, the machine learning model being pre-trained based on a plurality of past scans and corresponding reports composed based on the past scans, the past scans comprising at least some scans of other subjects;
   based on the current report and the one or more scans of the subject, the machine learning model generating one or more suggestions for updating the text of the report; and
   outputting data to cause a user interface to display to the user one or more suggestions for updating the text of the current report, with each respective suggestion visually linked in the user interface to a corresponding subregion within at least one image of at least one of the one or more scans based upon which the respective suggestion was generated.

2. The method of claim 1, further comprising receiving back at least one update to the current report entered by the user through the user interface based on at least one of the one or more suggestions, and updating the current report with the at least one update to produce an updated report.

3. The method of claim 2, further comprising inputting the updated report into the machine model to generate one or more updated suggestions, and outputting data to cause the user interface to display the one or more updated suggestions to the user, each visually linked to a subregion within at least one image in at least one of the one or more scans based upon which the updated suggestion was generated.

4. The method of claim 3, further comprising receiving back at least one further update to the report entered by the user through the user interface based on at least one of the one or more further suggestions, and further updating the updated report with the at least one further update.

5. The method of claim 2, further comprising refining the training of the machine learning model based on the at least one update and/or further update.

6. The method of claim 1, wherein the method further comprises:
receiving one or more additional scans of the subject, taken after said one or more scans;
receiving a modified version of the current report having been modified by the user based on examining the one or more additional scans;
inputting the one or more additional scans and modified report to the machine learning model to generate one or more modified suggestions for updating the modified report; and
outputting data to cause the user interface to display the one or more modified suggestions to the user, each visually linked to a subregion within at least one image in at least one of the one or more additional scans based upon which the modified suggestion was generated.

7. The method of claim 6, further comprising: receiving back at least one additional update to the current report entered by the user through the user interface based on at least one of the one or more modified suggestions, and updating the current report with the at least one additional update.

8. The method of claim 6, further comprising refining the training the machine learning model based on the at least one additional update.

9. The method of claim 1, wherein the displaying of the one or more suggestions comprises displaying a marked-up version of at least some of the text of the current report with the one or more suggestions shown in-line.

10. The method of claim 1, wherein the visual linkage comprises displaying each of the one or more suggestions in association with a respective colour, and marking the corresponding subregion with substantially the same colour.

11. The method of claim 10, wherein the displaying of each of the one or more suggestions in association with a respective colour comprises: displaying the suggestion using text of the respective colour, highlighting the suggestion with the respective colour, or drawing a line around the suggestion.

12. The method of claim 10, wherein the marking of each subregion comprises: highlighting the subregion with the respective colour, or drawing a line of the respective colour around the subregion.

13. The method of claim 1, wherein the visual linking comprises displaying a respective reference sign in association with each of the one or more suggestions, and displaying substantially the same reference sign in association with the corresponding subregion.

14. The method of claim 1, wherein the generating and displaying of the one or more suggestions comprises generating and displaying at least one of the suggestions live as the user composes the report.

15. The method of claim 1, wherein each of the scans comprises one of: an x-ray based scan, a PET scan, an MRI scan, or an ultrasound scan.

16. The method of claim 1, wherein at least one of the scans comprises a 3D scan comprising a stack of images showing different cross-sectional slices through the part of the subject.

17. The method of claim 1, wherein one or both of:
the user interface enables the user to select one of the suggestions and in response indicates the subregion of the image based upon which the selected suggestion was generated; and/or
the user interface enables the user to select one of the subregions in one of the images and in response indicates the suggestion in the report generated based on the selected subregion.

18. The method of claim 1, wherein the method further comprises applying the machine learning model to review a historical scan of the subject or another subject, together with a corresponding historical report authored based on the historical scan, to identify one or more possible errors in the historical report.

19. A computer program embodied on non-transitory computer-readable storage, configured so as when run on one or more processors to perform operations of:
receiving a current report on a condition of a human or animal subject, the current report comprising text composed by a user based on examining one or more scans of the subject, each of the one or more scans comprising at least one image of at least part of the subject;
receiving the one or more scans;
inputting the current report and the one or more scans into a trained machine learning model, the machine learning model being pre-trained based on a plurality of past scans and corresponding reports composed based on the past scans, the past scans comprising at least some scans of other subjects;
based on the current report and the one or more scans of the subject, the machine learning model generating one or more suggestions for updating the text of the report; and
outputting data to cause a user interface to display to the user one or more suggestions for updating the text of the current report, with each respective suggestion visually linked in the user interface to a corresponding subregion within at least one image of at least one of the one or more scans based upon which the respective suggestion was generated.

20. A computer system comprising:
processing apparatus comprising one or more processors; and
memory comprising one or more memory units, the memory storing code arranged to run on the processing apparatus, wherein the code is configured so as when run on the processing apparatus to perform operations of:
receiving a current report on a condition of a human or animal subject, the current report comprising text composed by a user based on examining one or more scans of the subject, each of the one or more scans comprising at least one image of at least part of the subject;

receiving the one or more scans;

inputting the current report and the one or more scans into a trained machine learning model, the machine learning model being pre-trained based on a plurality of past scans and corresponding reports composed based on the past scans, the past scans comprising at least some scans of other subjects;

based on the current report and the one or more scans of the subject, the machine learning model generating one or more suggestions for updating the text of the report; and outputting data to cause a user interface to display to the user one or more suggestions for updating the text of the current report, with each respective suggestion visually linked in the user interface to a corresponding subregion within at least one image of at least one of the one or more scans based upon which the respective suggestion was generated.

\* \* \* \* \*